United States Patent

Timmler et al.

[11] 4,140,782
[45] Feb. 20, 1979

[54] COMBATING FUNGI AND NEMATODES WITH DIPHENYL-TRIAZOLYL-METHANES

[75] Inventors: Helmut Timmler; Wilfried Draber; Karl H. Buchel; Wolfgang Kramer, all of Wuppertal; Wilhelm Brandes, Cologne; Paul-Ernst Frohberger; Bernhard Homeyer, both of Leverkusen, all of Fed. Rep. of Germany

[73] Assignee: Bayer Aktiengesellschaft, Leverkusen, Fed. Rep. of Germany

[21] Appl. No.: 806,889

[22] Filed: Jun. 15, 1977

[30] Foreign Application Priority Data

Jun. 23, 1976 [DE] Fed. Rep. of Germany ....... 2628152

[51] Int. Cl.² .......................... A01N 9/00; A01N 9/22
[52] U.S. Cl. .................................. 424/269; 260/308 R
[58] Field of Search ......................... 424/269

[56] References Cited

FOREIGN PATENT DOCUMENTS 2037610  2/1972  Fed. Rep. of Germany.
1795249  11/1975  Fed. Rep. of Germany.

Primary Examiner—Allen J. Robinson
Attorney, Agent, or Firm—Sprung, Felfe, Horn, Lynch & Kramer

[57] ABSTRACT

Diphenyl-triazolyl-methanes of the formula

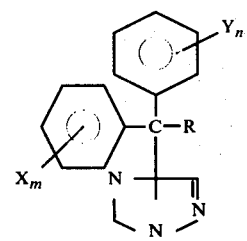

(I), in which
R is alkyl, alkylcarbonyl or optionally substituted phenylcarbonyl,
X and Y each independently is halogen, alkyl, halogenoalkyl, alkoxy, alkylthio, optionally substituted phenyl or phenoxy, nitro or cyano, and
m and n each independently is an integer from 0 to 5, and their physiologically tolerated salts are used to combat fungi and nematodes.

9 Claims, No Drawings

COMBATING FUNGI AND NEMATODES WITH DIPHENYL-TRIAZOLYL-METHANES

The present invention relates to and has for its objects the combating of fungi and nematodes with diphenyl-triazolyl-methanes, and active compositions in the form of mixtures of such compounds with solid and liquid dispersible carrier vehicles, with other and further objects becoming apparent from a study of the within specification and accompanying examples.

It has been disclosed in German Published Specification No. 1,795,249 that certain trityl-1,2,4-triazoles, such as triphenyl-(1,2,4-triazol-1-yl)-methane (Compound A), possess a good fungicidal activity. Their action is, however, not always entirely satisfactory, especially if low amounts and low concentrations are used.

It has been found that the diphenyl-triazolyl-methanes of the general formula

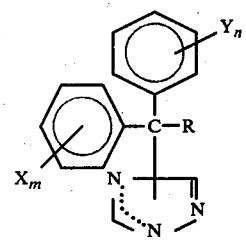

(I), in which
  R is alkyl, alkylcarbonyl or optionally substituted phenylcarbonyl,
  X and Y each independently is halogen, alkyl, halogenoalkyl, alkoxy, alkylthio, optionally substituted phenyl or phenoxy, nitro or cyano, and
  m and n each independently is an integer from 0 to 5,
and their physiologically tolerated salts, exhibit powerful fungicidal and nematicidal properties.

Surprisingly, the active compounds which can be used according to the invention exhibit a substantially greater fungicidal action than the trityl-1,2,4-triazoles known from the state of the art, such as, for example, triphenyl-(1,2,4-triazol-1-yl)-methane. Their additional nematicidal action is equally surprising. Accordingly, the compounds which can be used according to the invention represent an enrichment of the art.

It is to be understood that the use of a mixture of two or more bases (I), of two or more salts or of at least one base (I) and at least one salt is comprehended herein.

The diphenyl-triazoly-methanes of the general formula (I) are derivatives of 1,2,4-triazole in which the azole radical may be linked in the 1-position or in the 4-position.

Preferably, R represents alkyl with 1 to 4 carbon atoms, alkylcarbonyl with 1 to 4 carbon atoms in the alkyl part or phenylcarbonyl which is optionally substituted by halogen (especialy fluorine, chlorine or bromine) or by alkyl with 1 or 2 carbon atoms, X and Y, which may be identical or different, each represents halogen (especially fluorine, chlorine or bromine), straight-chain or branched alkyl with 1 to 4 carbon atoms, halogenoalkyl with 1 to 4 carbon atoms and up to 5 halogen atoms (especially with 1 or 2 carbon atoms and up to 3 identical or different halogen atoms, the preferred halogens being fluorine and chlorine and the trifluoromethyl group being mentioned as an example), cyano, nitro, alkoxy with 1 or 2 carbon atoms, alkylthio with 1 or 2 carbon atoms or phenyl or phenoxy, either of which is optionally substituted by halogen (especially fluorine, chlorine or bromine) or by alkyl with 1 or 2 carbon atoms, and m and n represent 0, 1, 2 or 3 (especially 0, 1 or 2).

The following may be mentioned as individual examples of the active compounds which can be used according to the invention: 1,1-diphenyl-1-(1,2,4-triazol-1-yl)-ethane, 1,1-diphenyl-1-(1,2,4-triazol-4-yl)-ethane, 1-(4-chlorophenyl)-1-(1,2,4-triazol-1-yl)-ethane, 1-(4-chlorophenyl)-1-phenyl-1-(1,2,4-triazol-4-yl)-ethane, 2-(2,4-dichlorophenyl)-1-phenyl-1-(1,2,4-triazol-1-yl)-ethane, 1-(4-fluorophenyl)-1-phenyl-1-(1,2,4-triazol-1-yl)-ethane, 1-(2-methylphenyl)-1-phenyl-1-(1,2,4-triazol-1-yl)-ethane, 1-(3-trifluoromethylphenyl)-1-phenyl-1-(1,2,4-triazol-1-yl)-ethane, 1-(4-methoxyphenyl)-1-phenyl-1-(1,2,4-triazol-1-yl)-ethane, 1-(4-methylthiophenyl)-1-phenyl-1-(1,2,4-triazol-1-yl)-ethane, 1-(4-biphenylyl)-1-phenyl-1-(1,2,4-triazol-1-yl)-ethane, 1-(4-biphenylyl)-1-phenyl-1-(1,2,4-triazol-4-yl)-ethane, 1-(4'-chlorobiphenylyl)-1-phenyl-1-(1,2,4-triazol-1-yl)-ethane, 1-(4-phenoxyphenyl)-1-phenyl-1-(1,2,4-triazol-1-yl)-ethane, 1,1-diphenyl-1-(1,2,4-triazol-1-yl)-propane, 1,1-diphenyl-1-(1,2,4-triazol-4-yl)-propane, 1-(4-chlorophenyl)-1-phenyl-1-(1,2,4-triazol-1-yl)-propane, 1-(4-chlorophenyl)-1-phenyl-1-(1,2,4-triazol-4-yl)-propane, 1-(4-fluorophenyl)-1-phenyl-1-(1,2,4-triazol-1-yl)-propane, 1-(3-methylphenyl)-1-phenyl-1-(1,2,4-triazol-1-yl)-propane, 1-(3,4-dimethylphenyl)-1-phenyl-1-(1,2,4-triazol-1-yl)-propane, 1-(2,5-dimethylphenyl)-1-phenyl-1-(1,2,4-triazol-1-yl)-propane, 1,1-diphenyl-1-(1,2,4-triazol-1-yl)-butane, 1,1-diphenyl-1-(1,2,4-triazol-4-yl)-butane, 1-(4-chlorophenyl)-1-phenyl-1-(1,2,4-triazol-1-yl)-butane, 1-(4-chlorophenyl)-1-phenyl-1-(1,2,4-triazol-4-yl)-butane, 1-(4-fluorophenyl)-1-(1,2,4-triazol-1-yl)-butane, 1-(3-methylphenyl)-1-phenyl-1-(1,2,4-triazol-1-yl)-butane, 1-(3-trifluoromethylphenyl)-1-phenyl-1-(1,2,4-triazol-1-yl)-butane, 1,1-diphenyl-2-methyl-1-(1,2,4-triazol-1-yl)-propane, 1,1-diphenyl-1-(1,2,4-triazol-1-yl)-pentane, 1-(2-chlorophenyl)-1-phenyl-1-(1,2,4-triazol-1-yl)-pentane, 1-(4-fluorophenyl)-1-phenyl-1-(1,2,4-triazol-1-yl)-pentane, 1-(3-methylphenyl)-1-phenyl-1-(1,2,4-triazol-1-yl-pentane, 1,1-diphenyl-2-methyl-1-(1,2,4-triazol-1-yl)-butane, 1-(4-chlorophenyl)-1-phenyl-2-methyl-1-(1,2,4-triazol-1-yl)-butane, 1-(4-fluorophenyl)-1-phenyl-2-methyl-1-(1,2,4-triazol-1-yl)-butane, 1-(2-methylphenyl)-1-phenyl-2-methyl-1-(1,2,4-triazol-1-yl)-butane, 1-(2,4-dimethylphenyl)-1-phenyl-2-methyl-1-(1,2,4-triazol-1-yl)-butane, 1,1-diphenyl-2,2-dimethyl-1-(1,2,4-triazol-1-yl)-propane, 1,1-diphenyl-2,2-dimethyl-1-(1,2,4-triazol-4-yl)-propane, 1-(2-chlorophenyl)-2-phenyl-2,2-dimethyl-1-(1,2,4-triazol-1-yl)-propane, 1-(2-chlorophenyl)-1-phenyl-2,2-dimethyl-1-(1,2,4-triazol-4-yl)-propane, 1-(4-chlorophenyl)-1-phenyl-2,2-dimethyl-1-(1,2,4-triazol-1-yl)-propane, 1-(4-chlorophenyl)-1-phenyl-2,2-dimethyl-1-(1,2,4-triazol-4-yl)-propane, 1-(4-fluorophenyl)-1-phenyl-2,2-dimethyl-1-(1,2,4-triazol-1-yl)propane, 1-(3-trifluoromethylphenyl)-1-phenyl-2,2-dimethyl-1-(1,2,4-triazol-1-yl)-propane, 1-(2-methylphenyl)-1-phenyl-2,2-dimethyl-1-(1,2,4-triazol-1-yl)-propane, 1-(3-methylphenyl)-1-phenyl-2,2-dimethyl-1-(1,2,4-triazol-1-yl)-propane, 1-(4-methoxyphenyl)-1-phenyl-2,2-dimethyl-1-(1,2,4-triazol-1-yl)-propane, 1-(4-ethyloxyphenyl)-1-phenyl-2,2-dimethyl-1-(1,2,4-triazol-1-yl)-propane, 1-(4-methylthiophenyl)-1-phenyl-2,2- dimethyl-1-(1,2,4-triazol-1-yl)-propane, 1-(4-chloro-3-methylphenyl)-1-phenyl-2,2-dimethyl-1-(1,2,4-triazol-1-yl)-propane, 1-(3,4-dimethylphenyl)-1-phenyl-2,2-dimethyl-1-(1,2,4-triazol-1-yl)-propane, 1-(2,4-dimethylphenyl)-1-phenyl-2,2-dimethyl-1-(1,2,4-triazol-1-yl)-propane, 1-(4-phenoxyphenyl)-1-phenyl-2,2-dimethyl-1-(1,2,4-triazol-1-yl)propane, 1-(4-4'-chlorophenoxyphenyl)-1-phenyl-2,2-dimethyl-1-(1,2,4-triazol-1-yl)-propane, 1-(4-biphenylyl)-1-phenyl-2,2-dimethyl-1-(1,2,4-triazol-1-yl)-propane, 1-(4-biphenylyl)-1-phenyl-2,2-dimethyl-1-(1,2,4-triazol-4-yl)-propane, 1-(4-4'-chlorobiphenylyl)-1-phenyl-2,2-dimethyl-1-(1,2,4-triazol-1-yl)-propane, 1-(2,4-dichlorphenyl)-1-phenyl-2,2-dimethyl-1-(1,2,4-triazol-1-yl)-propane, 1-(4-nitrophenyl)-1-phenyl-2,2-dimethyl-1-(1,2,4-triazol-1-yl)-propane, 1-(4-cyanophenyl)-1-phenyl-2,2-dimethyl-1-(1,2,4-triazol-1-yl)-propane, 1-bis-(4-chlorophenyl)-2,2-dimethyl-1-(1,2,4-triazol-1-yl)-propane, 1-bis-(4-chlorophenyl)-2,2-dimethyl-1-(1,2,4-triazol-4-yl)-propane, 1-bis-(4-methylphenyl)-2,2-dimethyl-1-(1,2,4-triazol-1-yl)-propane, 1-(4-chlorophenyl)-1-(4-fluorophenyl)-2,2-dimethyl-1-(1,2,4-triazol-1-yl)-propane, 1-(4-fluorophenyl)-1-(4-phenoxyphenyl)-2,2-dimethyl-1-(1,2,4-triazol-1-yl)-propane, 1-(4-biphenylyl)-1-(4-phenoxyphenyl)-2,2-dimethyl-1-(1,2,4-triazol-1-yl)-propane, 1,1-diphenyl-1-(1,2,4-triazol-1-yl)-propan-2-one, 1,1-diphenyl-1-(1,2,4-triazol-4-yl)-propan-2-one, 1-(4-chlorophenyl)-1-phenyl-1-(1,2,4-triazol-1-yl)-propan-2-one, 1-(4-chlorophenyl)-1-phenyl-1-(1,2,4-triazol-4-yl)-propan-2-one, 1-(2,4-dichlorophenyl)-1-phenyl-1-(1,2,4-triazol-1-yl)-propan-2-one, 1-(4-fluorophenyl)-1-phenyl-1-(1,2,4-triazol-1-yl)-propan-2-one, 1-(2-methylphenyl)-1-phenyl-1-(1,2,4-triazol-1-yl)-propan-2-one, 1-(3-trifluoromethylphenyl)-1-phenyl-1-(1,2,4-triazol-1-yl)-propan-2-one, 1-(4-methoxyphenyl)-1-phenyl-1-(1,2,4-triazol-1-yl)-propan-2-one, 1-(4-methylthiophenyl)-1-phenyl-1-(1,2,4-triazol-1-yl)-propan-2-one, 1-(4-biphenylyl)-1-phenyl-1-(1,2,4-triazol-1-yl)-propan-2-one, 1-(4-biphenylyl)-1-phenyl-1-(1,2,4-triazol-4-yl)-propan-2-one, 1-(4-4'-chlorobiphenylyl)-1-phenyl-1-(1,2,4-triazol-1-yl)-propan-2-one, 1-(4-phenoxyphenyl)-1-phenyl-1-(1,2,4-triazol-1-yl)-propan-2-one, 1,1-diphenyl-1-(1,2,4-triazol-1-yl)-butan-2-one, 1,1-diphenyl-1-(1,2,4-triazol-4-yl)-butan-2-one, 1-(4-chlorophenyl)-1-phenyl-1-(1,2,4-triazol-1-yl)-butan-2-one, 1-(4-chlorophenyl)-1-phenyl-1-(1,2,4-triazol-4-yl)-butan-2-one, 1-(4-fluorophenyl)-1-phenyl-1-(1,2,4-triazol-1-yl)-butan-2-one, 1-(3-methylphenyl)-1-phenyl-1-(1,2,4-triazol-1-yl)-butan-2-one, 1-(3,4-dimethylphenyl)-1-phenyl-1-(1,2,4-triazol-1-yl)-butan-2-one, 1-(2,5-dimethylphenyl)-1-phenyl-1-(1,2,4-triazol-1-yl)-butan-2-one, 1,1-diphenyl-1-(1,2,4-triazol-1-yl)-pentan-2-one, 1,1-diphenyl-1-(1,2,4-triazol-4-yl)-pentan-2-one, 1-(4-chlorophenyl)-1-phenyl-1-(1,2,4-triazol-1-yl)-pentan-2-one, 1-(4-chlorophenyl)-1-phenyl-1-(1,2,4-triazol-4-yl)pentan-2-one, 1-(4-fluorophenyl)-1-(1,2,4-triazol-1-yl)-pentan-2-one, 1-(3-methylphenyl)-1-phenyl-1-(1,2,4-triazol-1-yl)-pentan-2-one, 1-(3-trifluoromethylphenyl)-1-phenyl-1-(1,2,4-triazol-1-yl)-pentan-2-one, 1,1-diphenyl-3-methyl-1-(1,2,4-triazol-1-yl)-butan-2-one, 1,1-diphenyl-1-(1,2,4-triazol-1-yl)-hexan-2-one, 1-(2-chlorophenyl)-1-phenyl-1-(1,2,4-triazol-1-yl)-hexan-2-one, 1-(4-fluorophenyl)-1-phenyl-1-(1,2,4-triazol-1-yl)-hexan-2-one, 1-(3-methylphenyl)-1-phenyl-1-(1,2,4-triazol-1-yl)-hexan-2-one, 1,1-diphenyl-3-methyl-1-(1,2,4-triazol-1-yl)-pentan-2-one, 1-(4-chlorophenyl)-1-phenyl-3-methyl-1-(1,2,4-triazol-1-yl)-pentan-2-one, 1-(4-fluorophenyl)-1-phenyl-3-methyl-1-(1,2,4-triazol-1yl)-pentan-2-one, 1-(2-methylphenyl)-1-phenyl-3-methyl-1-(1,2,4-triazol-1-yl)-pentan-2-one, 1-(2,4-dimethylphenyl)-1-phenyl-3-methyl-1-(1,2,4-triazol-1-yl)-pentan-2-one, 1,1-diphenyl-3,3-dimethyl-1-(1,2,4-triazol-1-yl)-butan-2-one, 1,1-diphenyl-3,3-dimethyl-1-(1,2,4-triazol-4-yl)-butan-2-one, 1-(2-chlorophenyl)-1-phenyl-3,3-dimethyl-1-(1,2,4-triazol-1-yl)-butan-2-one, 1-(2-chlorophenyl)-1-phenyl-3,3-dimethyl-1-(1,2,4-triazol-4-yl)-butan-2-one, 1-(4-chlorophenyl)-1-phenyl-3,3-dimethyl-1-(1,2,4-triazol-1-yl)-butan-2-one, 1-(4-chlorophenyl)-1-phenyl-3,3-dimethyl-1-(1,2,4-triazol-4-yl)-butan-2-one, 1-(4-fluorophenyl)-1-phenyl-3,3-dimethyl-1-(1,2,4-triazol-1-yl)butan-2-one, 1-(3-trifluoromethylphenyl)-1-phenyl-3,3-dimethyl-1-(1,2,4-triazol-1-yl)-butan-2-one, 1-(2-methylphenyl)-1-phenyl-3,3-dimethyl-1-(1,2,4-triazol-1-yl)-butan-2-one, 1-(3-methylphenyl)-1-phenyl-3,3-dimethyl-1-(1,2,4-triazol-1-yl)-butan-2-one, 1-(4-methoxyphenyl)-1-phenyl-3,3-dimethyl-1-(1,2,4-triazol-1-yl)-butan-2-one, 1-(4-ethoxyphenyl)-1-phenyl-3,3-dimethyl-1-(1,2,4-triazol-1-yl)-butan-2-one, 1-(4-methylthiophenyl)-1-phenyl-3,3-dimethyl-1-(1,2,4-triazol-1-yl)-butan-2-one, 1-(4-chloro-3-methylphenyl)-1-phenyl-3,3-dimethyl-1-(1,2,4-triazol-1-yl)-butan-2-one, 1-(3,4-dimethylphenyl)-1-phenyl-3,3-dimethyl-1-(1,2,4-triazol-1-yl)-butan-2-one, 1-(2,4-dimethylphenyl)1-phenyl-3,3-dimethyl-1-(1,2,4-triazol-1-yl)-butan-2-one, 1-(4-phenoxyphenyl)-1-phenyl-3,3-dimethyl-1-(1,2,4-triazol-1-yl)-butan-2-one, 1-(4-4'-chlorophenoxyphenyl)-1-phenyl-3,3-dimethyl-1-(1,2,4-triazol-1-yl)-butan-2-one, 1-(4-biphenylyl)-1-phenyl-3,3-dimethyl-1-(1,2,4-triazol-1-yl)-butan-2-one, 1-(4-biphenylyl)-1-phenyl-3,3-dimethyl-1-(1,2,4-triazol-4-yl)-butan-2-one, 1-(4-4'-chlorobiphenylyl)-1-phenyl-3,3-dimethyl-1-(1,2,4-triazol-1-yl)-butan-2-one, 1-(2,4-dichlorophenyl)-1-phenyl-3,3-dimethyl-1-(1,2,4-triazol-1-yl)-butan-2-one, 1-(nitrophenyl)-1-phenyl-3,3-dimethyl-1-(1,2,4-triazol-1-yl)-butan-2-one, 1-(4-cyanophenyl)-3,3-dimethyl-1-(1,2,4-triazol-1-yl)-butan-2-one, 1-bis-(4-chlorophenyl)-3,3-dimethyl-1-(1,2,4-triazol-1-yl)-butan-2-one, 1-bis-(4-chlorophenyl)-3,3-dimethyl-1-(1,2,4-triazol-4-yl)-butan-2-one, 1-bis-(4-methylphenyl)-3,3-dimethyl-1-(1,2,4-triazol-1-yl)-butan-2-one, 1-(4-chlorophenyl)-1-(4-fluorophenyl)-3,3-dimethyl-1-(1,2,4-triazol-1-yl)-butan-2-one, 1-(4-fluorophenyl)-1-(4-phenoxyphenyl)-3,3-dimethyl-1-(1,2,4-triazol-1-yl)-butan-2-one, 1-(4-biphenylyl)-1-(4-phenoxyphenyl)-3,3-dimethyl-1-(1,2,4-triazol-1-yl)-butan-2-one, benzoyl-diphenyl-1,2,4-triazol-1-yl-methane, benzoyl-diphenyl-1,2,4-triazol-4-yl-methane, benzoyl-(4-chlorophenyl)-phenyl-1,2,4-triazol-1-yl-methane, benzoyl-(4-chlorophenyl)-phenyl-1,2,4-triazol-4-yl-methane, benzoyl-(4-fluorophenyl)-phenyl-1,2,4-triazol-1-yl-methane, benzoyl-(3-trifluoromethylphenyl)-phenyl-1,2,4-triazol-1-yl-methane, benzoyl-(3-methylphenyl)-phenyl-1,2,4-triazol-1-yl-methane, benzoyl-(4-methoxyphenyl)-phenyl-1,2,4-triazol-1-yl-methane, benzoyl-(3,4-dimethylphenyl)-phenyl-1,2,4-triazol-1-yl-methane, benzoyl-(4-chloro-3-methylphenyl)-phenyl-1,2,4-triazol-1-yl-methane, benzoyl-(4-phenoxyphenyl)-phenyl-1,2,4-triazol-1-yl-methane, benzoyl-(4,4'-chlorophenoxyphenyl)-phenyl-1,2,4-triazol-1-yl-methane, benzoyl-(4-biphenylyl)-phenyl-1,2,4-triazol-1-yl-methane, benzoyl-(4-4'-chlorobiphenylyl)-phenyl-1,2,4-triazol-1-yl-methane, benzoyl-(2,4-dichlorophenylyl)-phenyl-1,2,4-triazol-1-yl-methane, benzoyl-bis-(4-chlorophenyl)-1,2,4-triazole-1yl-methane, benzoyl-bis-(4-methylphenyl)-1,2,4-triazol-1-yl-methane, benzoyl-(4-chlorophenyl)-(4-fluorophenyl)-1,2,4-triazol-1-yl-methane, benzoyl-(4-fluorophenyl)-(4-phenoxyphenyl)-1,2,4-triazol-1-yl-methane, benzoyl-(4-bisphenylyl)-(4-phenoxyphenyl)-1,2,4-triazol-1-yl-methane, (4-chlorobenzoyl)-diphenyl-1,2,4-triazol-1-yl-methane, (4-chlorobenzoyl)-diphenyl-1,2,4-triazol-4-yl-methane, (4-chlorobenzoyl-(4-chlorophenyl)-phenyl-1,2,4-triazole-1-yl-methane, (4-chlorobenzoyl)-(4-fluorophenyl)-phenyl-1,2,4-triazol-1-yl-methane, (4-chlorobenzoyl)-(3-trifluoromethylphenyl)-phenyl-1,2,4-triazol-1-yl-methane, (4-chlorobenzoyl)-(3-methylphenyl)-phenyl-1,2,4-triazol-1-yl-methane, (4-chlorobenzoyl)-(4-phenoxyphenyl)-phenyl-1,2,4-triazole-1-yl-methane, (4-chlorobenzoyl)-(4-biphenylyl)-phenyl-1,2,4-triazol-1-yl-methane, (4-fluorobenzoyl)-diphenyl-1,2,4-triazol-1-yl-methane, (3-methylbenzoyl)-diphenyl-1,2,4-triazol-1-yl-methane, (4-fluorobenzoyl)-(4-chlorophenyl)-phenyl-1,2,4-triazol-1-yl-methane and (3-methylbenzoyl)-(4-chlorophenyl)-phenyl-1,2,4-triazol-1-yl-methane.

Some of the compounds which can be used according to the invention are known (see German Offenlegungsschrift (German Published Specification) No. 2,037,610). However, their use as fungicides and nematicides is new.

The majority of the compounds which can be used according to the invention are new; however, they can be prepared in a simple manner, in accordance with known processes. For example, they are obtained when the corresponding known diphenyl-halogeno-methanes are reacted with 1,2,4-triazole in the presence of an acid-binding agent, for example an excess of the triazole, and, if appropriate, in the presence of a polar organic solvent, for example acetonitrile, preferably in the temperature range between 20° and 100° C., and the product is isolated in accordance with customary methods. Further details relating thereto are to be found in the preparative examples given later in this text.

Suitable salts of the compounds of the formula (I) are salts wit physiologically tolerated acids, especially the hydrogen halide acids, for example hydrobromic acid and, especially, hydrochloric acid, phosphoric acid, nitric acid, monofunctional and bifunctional carboxylic acids and hydroxycarboxylic acids, such as, for example, acetic acid, maleic acid, succinic acid, fumaric acid, citric acid, salicyclic acid, sorbic acid, tartaric acid and lactic acid, and 1,5-naphthalenedisulphonic acid.

The salts of the compounds of the formula (I) can be obtained in a simple manner in accordance with customary methods of forming salts, for example by dissolving the base in ether, for example diethyl ether, and adding the acid, for example nitric acid, and can, using known methods, be isolated, for example by filtering off, and be purified if appropriate.

The active compounds according to the invention exhibit a powerful fungitoxic action and a bacteriotoxic action. They do not damage crop plants in the concentrations required for combating fungi and bacteria. For these reasons they are suitable for use as plant protection agents for combating fungi and bacteria. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, and also against seed-borne pathogens.

They display a particularly good activity against parasitic fungi on above-ground parts of plants, such as powdery mildew fungi, for example against species of Erysiphe and species of Podosphaera, and also against species of Venturia. In addition, they exhibit a high activity against cereal diseases, such as against cereal mildew and cereal rust. An aspect to be singled out particularly is that the active compounds according to the invention not only display a protective action, but are also curatively active, that is to say when used after infection has occurred. Furthermore, the systemic action of the compounds should be pointed out. Thus, it proves possible to protect plants against fungal attack by supplying the active compound to the above-ground parts of the plant through the soil and the root or through the seeds.

As plant protection agents, the compounds according to the invention can be used for the treatment of soil, the treatment of seed and the treatment of above-ground parts of plants. Because of their low odor and their good toleration by human skin, they are not unpleasant to handle.

When used as seed dressings, the compounds according to the invention are active against seed-borne plant diseases, namely by disinfecting the surface of the seed, for example when counteracting stripe disease of barley, and also systemically when counteracting fungal pathogens in the interior of the seed, as in the case of loose smuts of wheat and of barley. In addition, seed dressing achieves a systemic protective action against fungal infections of the shoot, for example against mildew.

The active compounds are also suitable for combating animal pests, especially nematodes, which occur in agriculture and in forestry. They are active against normally sensitive and resistant species and against all or some stages of development.

The plant-parasitic nematodes include Pratylenchus spp., *Radopholus similis, Ditylenchus dipsaci, Tylenchulus semipenetrans,* spp., Meloidogyne spp., Aphelenchoides spp., Longidorus spp., Xiphinema spp. and Trichodorus spp..

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for used as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, dichlorodifluoromethane, trichlorofluoromethane, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other fungicides and nematicides, or insecticides, acaricides, bactericides, rodenticides, herbicides, fertilizers, growth-regulating agents, bird repellants, plant nutrients, agents for improving soil structure, etc., if desired, or in the form of particular dosage preparations for specificf application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferentially 0.01–10%, by weight of the mixture. Thus, the present invention contemplates overall compositions which comprise mixtures of a conventional dispersibe carrier such as (1) a dispersible inert finely divided carrier solid, and/or (2) a dispersibe carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well-known ultra-low-volume process with good success, i.e. by applying such compound if normally a liquid, or by applying a liquid compositon containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Especially when used as leaf fungicides, the active compounds concentrations in the use forms can be varied within a fairly wide range. They are, in general, from 0.1 to 0.00001 per cent by weight, preferably from 0.05 to 0.0001 per cent.

For the treatment of seed, amounts of active compound of 0.001 to 50 g per kilogram of seed, preferably 0.01 to 10 g, are in general employed.

When used as nematicides, the active compound content can be varied within wide ranges. The active compound concentration of the use forms can be from 0.0000001 to 100% by weight of active compound, preferably from 0.01 to 10% by weight.

When used against nematodes, the preparations are generally applied to an area of agriculture in amounts of 1 to 100 kg of active compound per hectare, and are then incorporated into the soil.

When relatively high concentrations are used, the compounds usable according to the invention show plant growth-regulating properties.

Furthermore, the present invention contemplates methods of selectively killing, combating or controlling pests, e.g. fungi and nematodes, which comprises applying to at least one of correspondingly (a) such fungi, (b) such nematodes, and (c) the corresponding habitat thereof, i.e. the locus to be protected, e.g. to a growing crop, to an area where a crop is to be grown or to a domestic animal, a correspondingly combative or toxic amount, i.e. a fungicidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Erysiphe test (cucumbers)/protective

Solvent: 4.7 parts by weight of acetone
Emulsifier: 0.3 part by weight of alkylaryl polyglycol ether
Water: 95 parts by weight.

The amount of the active compund required for the desired concentration of active compound in the spray liquid was mixed with the stated amount of the solvent, and the concentrate was diluted with the stated amount of water containing the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoriacearum*. The plants were subsequently placed in a greenhouse at 23-24° C. and at a relative atmospheric humidity of about 75 %.

After 12 days, the infection of the cucumber plats was determined. The assessment data were converted to percent infection. 0% meant no infection; 100% meant that the plants were completely infected.

The active compounds, the concentrations of the active compounds and the results can be seen from the following table:

Table 1

| Erysiphe test (cucumbers)/protective | | | |
|---|---|---|---|
| | Infection in % at an active compound concentration of | | |
| Active compound | 0.00078 | 0.0005 | 0.00025 |
| (known) (A) | 63 | — | — |
| (5) | — | — | 0 |
| (2) | — | — | 0 |
| (3) | — | — | 22 |
| (1) | — | 17 | — |

Table 1-continued

| Erysiphe test (cucumbers)/protective | | | |
|---|---|---|---|
| | Infection in % at an active compound concentration of | | |
| Active compound | 0.00078 | 0.0005 | 0.00025 |

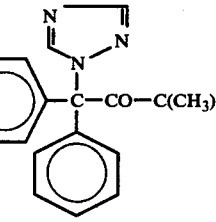
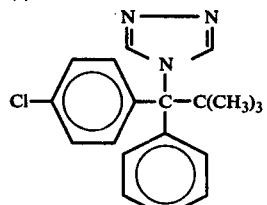

EXAMPLE 2

Shoot treatment test/cereal mildew (leaf-destructive mycosis)

To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis var. hordei*.

To test for curative activity the corresponding procedure was followed in converse sequence. The treatment of the single-leaved young barley plants with the prepartion of active compound was carried out 48 hours after inoculation, when the infection was already manifest.

After 6 days' dwell time of the plants at a temperature of 21-22° C. and 80-90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

The active compounds, active compound concentrations in the spray liquor and degrees of infection can be seen from the table which follows.

For the treatment of seed, barley seed was shaken with the extended active compound in a closed glass bottle. The seed was sown at the rate of 3 × 12 grains Table 2

Shoot treatment test/cereal mildew/protective/curative

| Active compounds | Active compound concentration in the spray liquor in % by weight | Infection in % of the untreated control protective | Infection in % of the untreated control curative |
|---|---|---|---|
| Untreated | — | 100.0 | 100.0 |
| (A) (known) — triazole-N-C(phenyl)$_3$ | 0.025 | 100.0 | 100.0 |
| (5) — Cl-phenyl, triazole-N-C(phenyl)(CO—C(CH$_3$)$_3$) | 0.025 | 0.0 | — |
| (2) — triazole-N-C(phenyl)$_2$(CO—C(CH$_3$)$_3$) | 0.025 | 0.0 | 0.0 |
| (3) — Cl-phenyl, imidazole-N-C(phenyl)(C(CH$_3$)$_3$) | 0.025 | 18.8 | 0.0 |
| (1) — triazole-N-C(phenyl)$_2$(C(CH$_3$)$_3$) | 0.025 | 0.0 | 0.0 |

EXAMPLE 3

Powdery mildew of barley test (*Erysiphe graminis var. hordei*)/systemic (fungal disease of cereal shoots)

The active compounds were used as pulverulent seed treatment agents. They were prepared by extending the particular active compound with a mixture of equal parts by weight of talc and kieselguhr to give a finely pulverulent mixture of the desired concentration of active compound.

in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of *Erysiphe graminis var. hordei* and grown further at 21-22° C. and 80-90% relative atmospheric humidity and 16 hours' exposure to light. The typical mildew pustules formed on the leaves over the course of 6 days.

The degree of infection was expressed as a percentage of the infection of the untreated control plants. Thus, 0% denoted no infection and 100% denoted the same degree of infection as in the case of the untreated control. The more active the compound, the lower was the degree of moldew infection.

The active compounds and concentrations of active compound in the seed treatment agent, as well as the amount used of the latter, and the percentage infection with mildew can be seen from the table which follows.

concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C. and 100% relative atmospheric humidity.

Table 3

| | Powdery mildew of barley test (*Erysiphe graminis var. hordei*)systemic | | |
|---|---|---|---|
| Active compounds | Active compound concentration in the dressing in % by weight | Amount of dressing used in g/kg of seed | Infection in % of the untreated control |
| Without dressing | — | — | 100.0 |
| 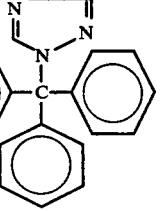 (A) (known) | 25 | 10 | 88.8 |
| 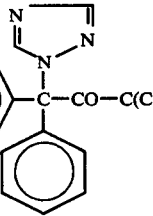 (2) | 25 | 10 | 0.0 |

EXAMPLE 4

Shoot treatment test/cereal rust/protective (leaf-destructive mycosis)

To produce a suitable preparation of active compound, 0.25 part by weight of active compound was taken up in 25 parts by weight of demethylformamide and 0.06 part by weight of alkylaryl polyglycol ether; 975 parts by weight of water were then added. The After 10 days' dwell time of the plants at a temperature of 20° C. and 80-90% atmospheric humidity, the occurrence of rust pustules on the plant was evaluated. The degree of infection was expressed as a percentage of the infection of the untreated control plants. 0% denoted no infection and 100% denoted the same degree of infection as in the case of the untreated control. The more active the compound, the lower was the degree of rust infection.

The active compounds, active compound concentrations in the spray liquor and degrees of infection can be seen from the table which follows.

Table 4

| | Shoot treatment test/cereal rust/protective | |
|---|---|---|
| Active compounds | Active compound concentration in the spray liquor in % by weight | Infection in % of the untreated control |
| Untreated | — | 100.0 |
| 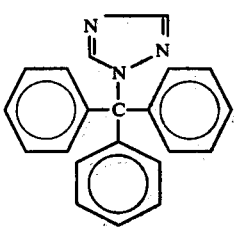 (A) (known) | 0.025 | 100.0 |

Table 4-continued

| Active compounds | Shoot treatment test/cereal rust/protective Active compound concentration in the spray liquor in % by weight | Infection in % of the untreated control |
|---|---|---|
| (5) Cl—C₆H₄—C(C₆H₅)(N-triazolyl)—CO—C(CH₃)₃ | 0.025 | 0.0 |
| (2) C₆H₅—C(C₆H₅)(N-triazolyl)—CO—C(CH₃)₃ | 0.025 | 13.8 |
| (3) Cl—C₆H₄—C(C₆H₅)(N-triazolyl)—C(CH₃)₃ | 0.025 | 17.5 |
| (1) C₆H₅—C(C₆H₅)(N-triazolyl)—C(CH₃)₃ | 0.025 | 0.0 |

EXAMPLE 5

Podosphaera test (powdery mildew of apples(/protective

Solvent: 4.7 parts by weight of acetone
Emulsifier: 0.3 parts by weight of alkylaryl polyglycolether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in 4-6 leaved stage were sprayed with the spray liquid until dripping wet. The plants remained in a greenhouse for 24 hours at 20° C. and at a relative atmospheric humidity of 70%. They were then inoculated by dusting with conidia of the apple powdery mildew causative organism (*podosphaera leucotricha*) and placed in a greenhouse at a temperature of 21 - 23° C. and at a relative atmospheric humidity of about 70%.

10 days after the inoculation, the infection of the seedlings was determined. The ratings obtained were converted to percentage infection. 0% meant no infection; 100% meant that the plants were completely infected.

The active compounds, the concentrations of the active compounds and the results can be seen from the following table.

Table 5

| Podosphaera test (powdery mildew of apples)/protective | | | |
|---|---|---|---|
| | Infection in % at an active compound concentration of | | |
| Active compound | 0.00039 | 0.00031 | 0.00025 |
| 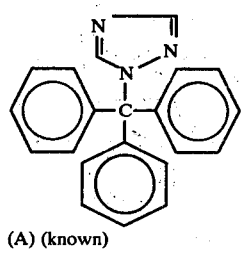 (A) (known) | 74 | — | |

Table 5-continued

*Podosphaera* test (powdery mildew of apples)/protective

| Active compound | Infection in % at an active compound concentration of | | |
|---|---|---|---|
| | 0.00039 | 0.00031 | 0.00025 |
| (5) Cl–C₆H₄–C(N-triazole)(C₆H₅)–CO–C(CH₃)₃ | — | 0 | — |
| (3) Cl–C₆H₄–C(N-triazole)(C₆H₅)–C(CH₃)₃ | — | 16 | — |

EXAMPLE 6

Test nematode: Meloidogyne incognita

Solvent: 3 parts by weight of acetone

Emulsifier: 1 part by weight of alkylaryl polyglycol ether

To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which ws heavily infested with the test nematodes. The concentration of the active compound in the preparation was of practically no importance; only the amount of active compound per unit volume of soil, which is given hereinafter in ppm (= mg/l), was decisive. The soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table.

Table 6

Nematicides
(*Meloidogyne incognita*)

| Active compound | Degree of destruction in % at an active compound concentration in ppm |
|---|---|
| | 20 ppm |
| (3) Cl–C₆H₄–C(N-triazole)(C₆H₅)–C(CH₃)₃ | 100 |

The preparation of the active compounds to be used according to this invention is illustrated by the following examples.

EXAMPLE 7

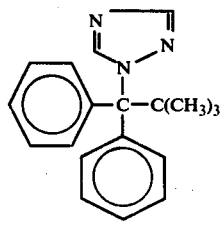

(1)

26.9 g (0.1 mol) of 1-chloro-2,2-dimethyl-1,2-diphenylpropane in 50 ml of acetonitrile were added dropwise, while stirring, to a boiling solution of 7 g (0.1 mol) of 1,2,4-triazole and 16 g of potassium carbonate in 200 ml of acetonitrile. The mixture was then heated for 48 hours under reflux. It was allowed to cool and was then filtered. The filtrate was concentrated by distilling off the solvent in vacuo. The residue was taken up in ethyl acetate, and the solution was repeatedly washed with water, dried over sodium sulphate and again concentrated by distilling off the solvent. The residue crystallized after addition of ligroin. After recrystallization from ligroin/ethyl acetate (6:1), 12 g (41% of theory) of 2,2-dimethyl-1,1-diphenyl-1-(1,2,4-triazol-1yl)-propane of melting point 137° C. were obtained.

EXAMPLE 8

(2)

51.3 g (0.15 mol) of 1-bromo-3,3-dimethyl-1,1-diphenylbutan-2-one in 250 ml of acetonitrile were added dropwise, while stirring, to a boiling solution of 25 g (0.36 mol) of 1,2,4-triazole in 250 ml of acetonitrile and heating under reflux was then continued for 24 hours. The mixture was then concentrated by distilling off the solvent in vacuo, the residue was taken up in ethyl acetate and the solution was repeatedly washed wth water, dried over sodium sulphate and concentrated by distilling off the solvent in vacuo. The residue crystallized after addition of ligroin. After recrystalization from ligroin, 19 g (40% of theory) of 3,3-dimethyl-1,1-diphenyl-1-(1,2,4-triazol-1-yl)-butan-2-one of melting point 99° C. were obtained.

The following compounds of the general formula

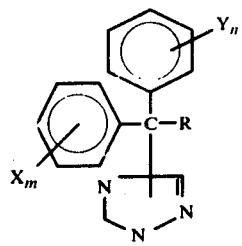

were obtained analogously to the above examples:

Table 7

| Compound No. | $X_m$ | $Y_n$ | R | Position where the 1,2,4-triazolyl radical is linked | Melting point (° C) |
|---|---|---|---|---|---|
| 3 | 4-Cl | — | C(CH$_3$)$_3$ | (4) | 155 |
| 4 | — | — | —CO—CH$_3$ | (1) | 168 |
| 5 | 4-Cl | — | CO—C(CH$_3$)$_3$ | (1) | 126 |

It will be appreciated that the instant specification and examples are set forth by way of illustration and not limitation, and that various modifications and changes may be made without departing from the spirit and scope of the present invention.

What is claimed is:

1. A fungicidal or nematicidal composition containing as active ingredient a fungicidally or nematicidally effective amount of a diphenyl-triazolyl-methane of the formula

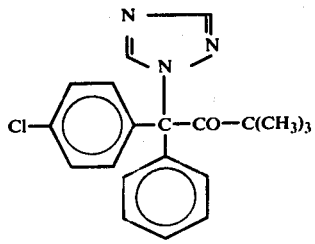

or a physiologically tolerated salt thereof, in admixture with a diluent.

2. A method of combating nematodes or fungi which comprises applying to plants, seed or soil, a nematicidally or fungicidally effective amount of a compound of the formula

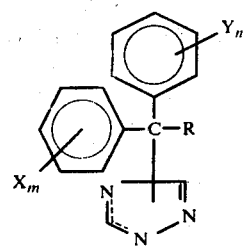

in which
R is alkyl with 1 to 4 carbon atoms, alkylcarbonyl with 1 to 4 carbon atoms in the alkyl part, or phenyl-carbonyl which is optionally substituted by halogen or by alkyl with 1 or 2 carbon atoms,
X and Y each independently is halogen, alkyl with 1 to 4 carbon atoms and up to 5 halogen atoms, cyano, nitro, alkoxy with 1 or 2 carbon atoms, alkylthio with 1 or 2 carbon atoms or phenyl or phenoxy, either of which is optionally substituted by halogen or by alkyl with 1 or 2 carbon atoms, and
m and n each independently is 0, 1, 2 or 3,
or a physiologically tolerated salt thereof.

3. A method according to claim 2, wherein the active ingredient is the compound of the formula

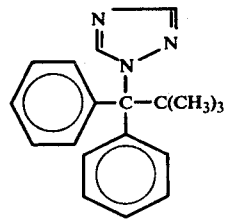

or a physiologically tolerated salt thereof.

4. A method according to claim 2, wherein the active ingredient is the compound of the formula

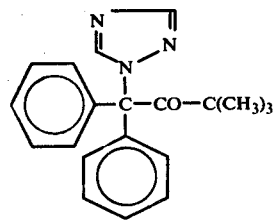

or a physiologically tolerated salt thereof.

5. A method according to claim 2, wherein the active ingredient is the compound of the formula

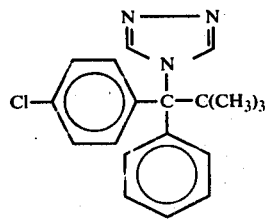

6. A method according to claim 2, wherein the active ingredient is the compound of the formula

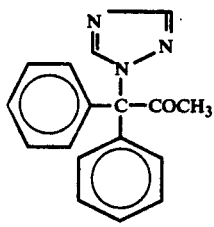

or a physiologically tolerated salt thereof.

7. A method according to claim 2, wherein the compond of the formula

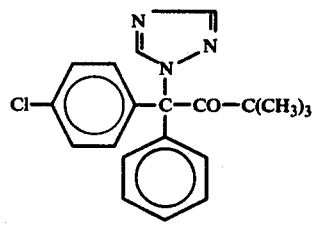

or a physiologically tolerated salt thereof.

8. The method according to claim 2, in which the active compound is applied to seed in an amount of 0.001 to 50 g per kg of seed.

9. The method according to claim 2, in which the active compound is

![structure](data:,) ![structure](data:,) ![structure](data:,) ![structure](data:,) ![structure](data:,)

or a physiologically tolerated salt thereof.

* * * * *